Oct. 19, 1971 D. L. ARMSTRONG Plant Pat. 3,075
ROSE PLANT
Filed Jan. 6, 1970
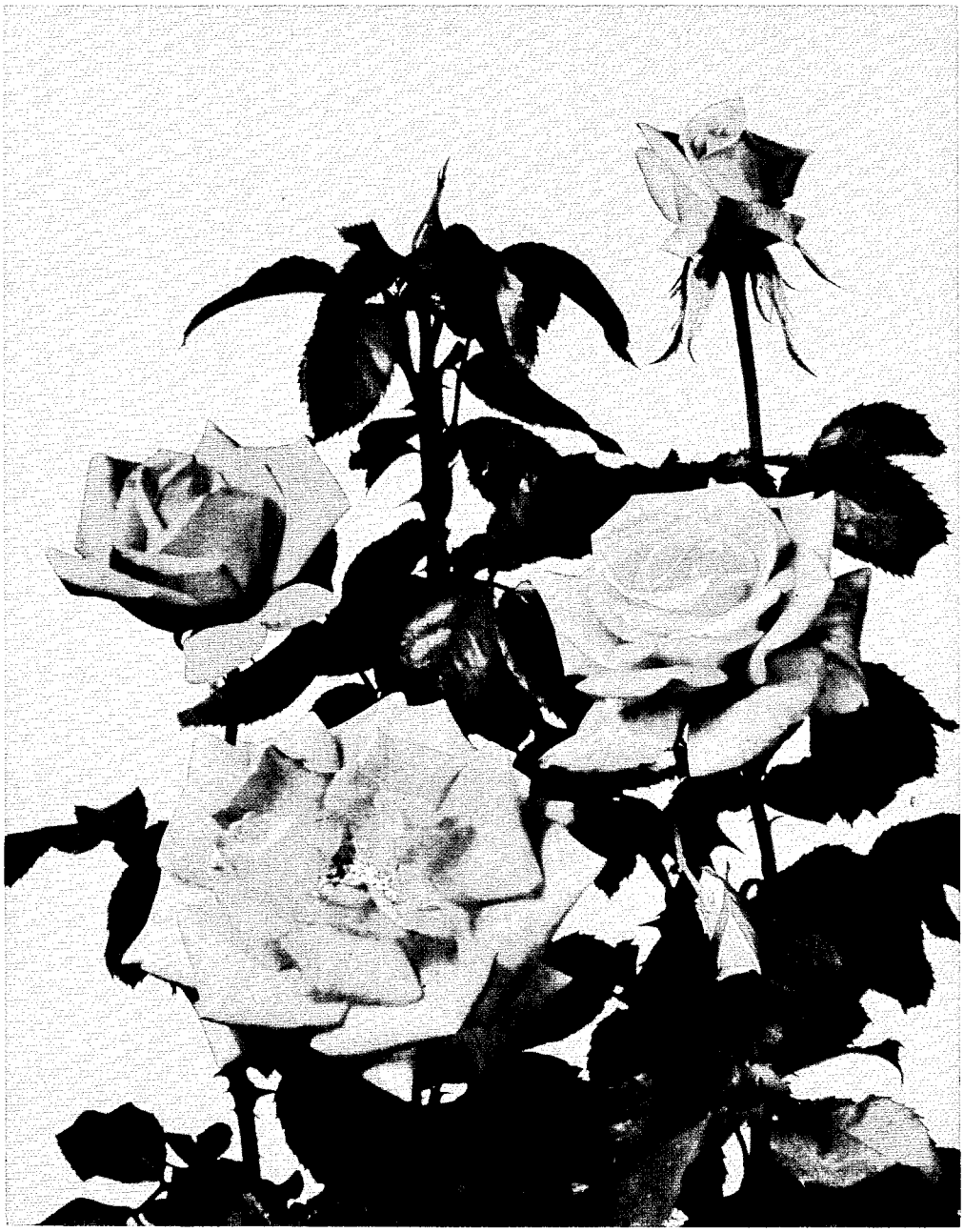

United States Patent Office

Plant Pat. 3,075
Patented Oct. 19, 1971

3,075
ROSE PLANT

David L. Armstrong, Upland, Calif., assignor to
Armstrong Nurseries, Inc., Ontario, Calif.

Filed Jan. 6, 1970, Ser. No. 1,065
Int. Cl. A01h 5/00
U.S. Cl. Plt.—20 1 Claim

ABSTRACT OF THE DISCLOSURE

A bush rose plant of the hybrid tea class which is tall growing and adapted for outdoor cultivation. The flowers are of average size for their class, with double petalage regularly arranged. The flowers are usually borne singly, but may appear in clusters of three or four on medium length stems of normal strength. The overall color effect is a strong reddish orange at first, tending towards a vivid red to strong red after a few days. The fragrance is subdued. The plant blooms abundantly outdoors, and blooms nearly continuously during the growing season. It is of upright-spreading habit, much branched.

This invention relates to a new variety of hybrid tea rose, having a tall bushy habit of growth, well adapted for outdoor cultivation, for cut flowers and garden decoration.

The plant, a seedling bred by crossing Fandango (P.P. 894) as the seed parent with Roundelay (P.P. 1,280) as the pollen parent, holds its distinguishing characteristics through succeeding propagations by cuttings and budding. It was originally propagated in Ontario, Calif.

The new variety is distinguished from its seed parent, Fandango, in several respects. The blooms of the present variety are classified as double, with 30 to 35 petals, plus petaloids, whereas Fandango is a semi-double flower with only 16 to 25 petals. Whereas Fandango is moderately fragrant, the new variety has very slight fragrance. The blooms of the new variety are primarily of an orange color tending into a vivid red, whereas Fandango gives the impression of a color which is commonly called "Turkey Red." Fandango will produce seed hips abundantly, out of doors. That is not true of the new variety. Whereas Fandango characteristically bears its flowers on erect stems, the new variety carries its flowers on stems which are often lax and sometimes nodding and semi-horizontal. The foliage of the new variety is not glossy, whereas the foliage of Fandango is glossy.

The new variety is distinguished from its pollen parent, Roundelay, in the following respects: Whereas Roundelay is of the grandiflora class, the new variety is typical of the hybrid tea class. Whereas blooms of the Roundelay plant have 35 to 40 petals, the new variety normally has from 30 to 35 petals. Although the blooms of both varieties are high centered at the beginning, the flowers of Roundelay develop to a flat pattern, whereas the flowers of the new variety progress to a cupped shape. The flower of Roundelay is normally 1" to 1½" smaller in diameter than the flower of the new variety. The fragrance of the flowers of the new variety is only slight, whereas the flowers of Roundelay are moderate but penetrating in fragrance. The growth habit of the Roundelay plant is upright and moderately stiff, whereas the habit of this new variety is more relaxed. Similarly, the petals of the Roundelay bloom are stiff and crisp, whereas the petals of the new variety are substantially less so. The petals of the new variety are substantially broader in relation to their length than are those of Roundelay.

Both the seed parent and the pollen parent exhibit a moderately stiff or quite stiff habit of growth, whereas the growth habit of the new variety is distinctly less stiff.

The accompanying drawing illustrates the plant in color, and shows the flowering thereof, from bud to full bloom.

The flowers of the new variety are usually borne singly, but sometimes there may be three or four upon a single stem in an irregular cluster. The stems are of normal strength and medium length. The bloom is abundant outdoors, and nearly continuous during the growing season. The fragrance, as indicated above, is slight.

In the description which follows, the color values stated conform to the Nickerson Color Fan.

*Bud*

As to the bud: The peduncle is of short to average length, and of average caliper, being erect and smooth, with few to several small stipitate glands and few, if any, small prickles. The color is near Light Olive, 10Y5/5, overlaid with near Moderate Reddish Brown, 10R3/4 on the side which is exposed to the sun.

Before the calyx breaks, the buds are of medium size and short to medium length, ovoid in form and without foliaceous appendages either on the surface of the bud or, generally, extending beyond the tip of the bud.

As the calyx breaks, the color is between Deep Purplish Red, 10RP3/10, and Dark Red, 2.5R3/7. The inner surface of the sepals is provided with a fine wooly tomentum. Margins of alternate sepals are likewise lined with fine wooly tomentum, but margins of other sepals carry from a few to several small stipitate glands and small slender foliaceous parts, although the sepals are usually without foliaceous appendages. The outside surface of the sepals is usually smooth.

As the first petal opens, the bud is of average size and short to medium length, being ovoid in form. Its color outside is between Strong Red, 2.5R5/12, and Strong Red, 5R4/12. There is a small area at the base of the petal which is near Vivid Yellow, 5Y8/12.

Inside, the coloration is between Strong Red, 2.5R5/12, and Vivid Red, 5R5/13. The small area at the base of the petal is near Vivid Yellow, 5Y8/12. The bud opens up well. It is not retarded or prevented from opening by cold, hot, wet, or dry weather.

*Bloom*

When fully open the blooms are of average size, ranging from 4" to 4½" in diameter. The petalage is double, displaying from 30 to 35 petals, plus 4 to 8 petaloids, regularly arranged. It is high centered at first, becoming cupped to high centered later on. The petals at first are tightly cupped with their tips reflexed outward. At maturity, the bloom becomes somewhat loosely cupped. Outside and intermediate petals of the newly opened flower are usually reflexed slightly outward both along the apex and along the edges of the petal. All petals of the three-days-open flower are usually reflexed slightly outward, both along the apex and edges of the petal.

*Petals*

The petals are of medium thick texture, moderately leathery, with inside satiny to velvety, and outside satiny also. The shape of the outside petals is between round and broadly obovate, with the apex flat and usually with one to three notches. The intermediate petals are likewise broadly obovate, with apex round and occasionally with one to two notches. The inside petals are likewise broadly obovate, with rounded apex. The colors may be modified by being shaded and/or washed with other colors.

The following description is of a newly opened flower grown outdoors during the month of September, in Ontario, Calif.:

The color of the outside petal on its outer surface was between Strong Red, 2.5R5/12, and Strong Purplish Red, 10RP5/12. The small area at the base of the petal was near Brilliant Yellow, 5Y9/9, both outside and inside the outer petals. The inside surface of the outer petals was between Deep Pink, 2.5R6/11, and Vivid Red, 5R5/13.

The color of the intermediate petals on the outer surface was between Strong Red, 2.5R5/12, and Vivid Red, 5R5/13. The small area at the base of the petal was near Brilliant Yellow, 5Y9/9. The inner surface of the intermediate petals was between Vivid Red, 5R5/13, and Strong Reddish Orange, 7.5R6/12. The small area at the base of the petal was near Vivid Yellow, 5Y8/12.

The color of the outer surface of the inner petals was between Strong Red, 2.5R5/12, and Vivid Red, 5R5/13. The small area at the base of the petal was near Brilliant Yellow, 5Y9/9. The inner surface of the inner petals was between Vivid Red, 5R5/13, and Strong Reddish Orange, 7.5R5/13. The small area at the base of the petal was near Vivid Yellow, 5Y8/12.

The following description is of a rose that had been open for three days outdoors in the month of September, in Ontario, Calif.:

The color of the outside petal, on its outer surface, was between Strong Red, 2.5R5/12, and Strong Purplish Red, 10RP5/12. The small area at the base of the petal was near Brilliant Greenish Yellow, 7.5Y9/8. The inner surface of the outer petals was between Deep Pink, 2.5R6/11, and Vivid Red, 5R5/13. The small area at the base of the petal was near Brilliant Greenish Yellow, 7.5Y9/8.

The color of the inside petal on its outer surface was near Strong Red, 2.5R5/12. The small area at the base of the petal was near Brilliant Greenish Yellow, 7.5Y9/8. The inner surface of the inside petals was between Strong Red, 2.5R5/12, and Vivid Red, 5R5/13. The small area at the base of the petal was near Brilliant Greenish Yellow, 7.5Y9/8.

The general color effect of the newly opened flower was between Vivid Red, 5R5/13, and Strong Reddish Orange, 7.5R5/13. After three days, the general color effect lay between Strong Red, 2.5R5/12, and Vivid Red, 5R5/13.

The blooms drop off cleanly and are not particularly affected by cold, hot, wet or dry weather.

The flower persists for three to four days in the month of November on bushes in the garden. Cut roses grown outdoors and kept at living room temperatures will last from two to three days in the month of November.

*Reproductive organs*

Stamens: Average in number, arranged regularly about the pistils, a few mixed with petaloids.

Filaments: Medium to long length (5 to 15 mm.), color near Strong Pink, 2.5R7/8, most with anthers.

Anthers: Small size, all open at about the same time. The margins of the anthers, upper and under sides, are near Strong Orange Yellow, 10YR7/10. The remainder of the anthers is near Moderate Purplish Pink, 2.58RP7/8, both above and below.

Pollen: Moderate to abundant, near Strong Orange Yellow, 7.5YR7/11, in color.

Pistils: Average to many in number (approximately 100).

Styles: Uneven, and short to average length, thin in caliper, and bunched. In color, the upper ⅔ is near Strong Purplish Red, 10RP4/12; the remainder is near Brilliant Greenish Yellow, 7.5Y9/8.

Stigma: Near Pale Orange Yellow, 7.5YR9/4, in color.

Ovaries: Usually all enclosed in the calyx.

Hips: No hips were observed on the plants grown at Ontario, Calif.

Sepals: Medium length, relatively straight, and falling soon.

*Foliage*

The leaves are compound with usually 3 to 7 leaflets. They are abundant in quantity and medium to large in size. They are somewhat leathery in texture and semi-glossy in appearance.

The leaflets are oval in shape, with apex acute and base round. The margins are simply serrate.

The color of the mature leaf on its upper surface is near Moderate Olive Green, 5GY4/3. The under surface is between Strong Yellow Green, 7.5GY6/8, and Moderate Yellow Green, 5GY5/6.

The color of the young foliage on the upper surface was near Moderate Olive Green, 7.5GY4/4, and the under surface near Moderate Yellow Green, 5GY5/6.

The rachis is of average size, being smooth and grooved on its upper side, with a few stipitate glands on its edges. The under side was smooth, with few, if any, small prickles.

The stipules are short to medium length, medium width, and with short to medium length points turning out at an angle of more than 45°.

The plant is mildly subject to mildew, as compared with other varieties now in commerce, when grown under comparable conditions at Ontario, Calif.

*Growth*

The plant is very free-growing, of an upright and spreading habit. It is much branched. The canes are medium to heavy in caliper.

The main stems are near Moderate Olive Green, 5GY4/3, carrying many large prickles of medium to long length, slightly hooked downward, and having medium length narrow bases. These prickles are between Strong Yellowish Brown, 7.5YR5/7, and Strong Yellowish Brown, 10YR5/6. There are many small prickles between Strong Yellowish Brown, 7.5YR5/7, and Strong Yellowish Brown, 10YR5/6. There are no hairs.

The branches are between Moderate Yellow Green, 7.5GY5/7, and Moderate Olive Green, 7.5GY4/4. They carry many large prickles which are long and almost straight, with short, narrow bases, and from several to many small prickles. The color of the prickles, both large and small, on the branches lies between Strong Yellowish Brown, 10YR5/6, and Moderate Brown, 7.5YR4/5. There are no hairs.

The new shoots are between Strong Yellow Green, 5GY6/8, and Moderate Yellow Green, 2.5GY5/5, overlaid with near Dark Red, 2.5F3/7, on the side exposed to the sun. The large prickles are several to many in number; they are of medium length, almost straight, with short, narrow bases; and near Dark Red, 5R3/7, in color. The small prickles on the new boots are few in number and near Dark Red, 5R3/7, in color. There are no hairs.

I claim:

1. An upright-spreading rose plant of the hybrid tea class, substantially as shown and described, said plant further having a novel combination of features including very free growth, heavy canes, and well-branched habit, said plant further tending to bear several blooms on single sturdy stems, the freshly-opened blooms being high centered, with petals tightly cupped, and orange red, almost vivid red, in color, the older blooms being loosely cupped and fading to strong red, the petals being well imbricated, of a leathery feel, and of satin or velvet texture.

No references cited.

ROBERT E. BAGWILL, Primary Examiner